United States Patent
Suzuki et al.

(10) Patent No.: US 10,429,233 B2
(45) Date of Patent: Oct. 1, 2019

(54) OBJECT INFORMATION OBTAINING DEVICE, DISPLAY METHOD, AND NON-TRANSITORY COMPUTER-READABLE STORAGE MEDIUM

(71) Applicant: CANON KABUSHIKI KAISHA, Tokyo (JP)

(72) Inventors: Koichi Suzuki, Kodaira (JP); Hiroshi Abe, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 15 days.

(21) Appl. No.: 15/700,996

(22) Filed: Sep. 11, 2017

(65) Prior Publication Data

US 2018/0010957 A1    Jan. 11, 2018

Related U.S. Application Data

(63) Continuation of application No. 14/134,957, filed on Dec. 19, 2013, now abandoned.

(30) Foreign Application Priority Data

Dec. 28, 2012  (JP) .................................. 2012-286685

(51) Int. Cl.
  *G01H 9/00* (2006.01)
  *A61B 5/00* (2006.01)
(52) U.S. Cl.
  CPC .............. *G01H 9/00* (2013.01); *A61B 5/0095* (2013.01)
(58) Field of Classification Search
  CPC ... A61B 5/0095; A61B 5/0035; A61B 5/0048; A61B 5/0059; A61B 5/0073;
  (Continued)

(56) References Cited

U.S. PATENT DOCUMENTS 5,588,032 A * 12/1996 Johnson ............... A61B 5/4312
  378/8
6,567,688 B1 * 5/2003 Wang ................... A61B 5/0095
  600/407

(Continued)

FOREIGN PATENT DOCUMENTS

JP        2005-218684 A    8/2005
JP        2010035806 A     2/2010

(Continued)

OTHER PUBLICATIONS

Xu, et al., "Universal back-projection algorithm for photoacoustic computed tomography", Physical Review E, (2005), pp. 016706-1-016706-7, vol. 71.

(Continued)

*Primary Examiner* — Aklilu K Woldemariam
(74) *Attorney, Agent, or Firm* — Canon U.S.A., Inc. IP Division

(57) ABSTRACT

An object information obtaining device includes a light source which emits light, an acoustic wave detecting unit which detects a photoacoustic wave generated by irradiation of an object with the light, and outputs an electric signal in response to detection of the photoacoustic wave, and a processing unit configured to perform two or more types of processing to photoacoustic signal data based on the electric signal to obtain object information corresponding to each of the two or more types of processing, and to display on a display unit the object information corresponding to at least one processing selected by a user out of the two or more types of processing.

20 Claims, 9 Drawing Sheets

(58) Field of Classification Search
CPC ... A61B 5/0097; A61B 5/14542; A61B 5/489;
A61B 5/743; A61B 5/05; A61B
2562/0204; A61B 2562/0233; G01N
21/1702; G01N 2021/1706; G01N
2291/02475; G01N 29/0672; G01N
29/2418; G01N 23/2055; G01N 29/0681;
G01H 9/00; G06T 11/60; G06T
2207/10072; G06T 2207/10088; G06T
2207/20221; G06T 2207/30068; G06T
5/009; G06T 5/50; G06T 7/33; G01S
15/8929; G06F 2203/04805; G06F
3/0481; G06K 2209/05; G06K 9/3233;
G02B 21/008; G10K 11/345
USPC .......... 382/128, 131; 378/37, 901; 600/407,
600/437; 715/772, 748, 769, 770, 771,
715/774
See application file for complete search history.

(56) References Cited

U.S. PATENT DOCUMENTS

| | | | |
|---|---|---|---|
| 6,891,920 B1 | 5/2005 | Minyard et al. | |
| 7,475,358 B2 | 1/2009 | Anzelde et al. | |
| 2005/0004458 A1* | 1/2005 | Kanayama | A61B 5/0091 600/437 |
| 2007/0140536 A1 | 6/2007 | Sehnert et al. | |
| 2009/0198128 A1* | 8/2009 | Fukutani | A61B 5/0091 600/437 |
| 2010/0094561 A1 | 4/2010 | Masumura | |
| 2010/0331662 A1* | 12/2010 | Fukutani | A61B 5/0059 600/407 |
| 2011/0106478 A1* | 5/2011 | Someda | A61B 5/0059 702/104 |
| 2011/0232385 A1* | 9/2011 | Nanaumi | A61B 5/0095 73/602 |
| 2011/0239766 A1* | 10/2011 | Nakajima | A61B 5/0073 73/587 |
| 2012/0239318 A1* | 9/2012 | Tokita | A61B 5/0091 702/56 |
| 2012/0259198 A1* | 10/2012 | Nagae | A61B 5/0095 600/407 |
| 2012/0302866 A1* | 11/2012 | Fukutani | A61B 5/0095 600/407 |
| 2013/0085371 A1* | 4/2013 | Miyasato | A61B 8/0825 600/407 |
| 2013/0267820 A1* | 10/2013 | Miyasato | A61B 5/0059 600/407 |
| 2014/0051969 A1* | 2/2014 | Suzuki | A61B 5/0095 600/407 |
| 2014/0182384 A1 | 7/2014 | Watanabe et al. | |

FOREIGN PATENT DOCUMENTS

| | | |
|---|---|---|
| JP | 2011-005237 A | 1/2011 |
| JP | 2011-125570 A | 6/2011 |
| JP | 2011120765 A | 6/2011 |
| JP | 2011143175 A | 7/2011 |
| JP | 2011-172611 A | 9/2011 |
| JP | 2012-061202 A | 3/2012 |
| JP | 2012135462 A | 7/2012 |
| WO | 2011048596 A1 | 4/2011 |
| WO | 2012138965 A2 | 10/2012 |
| WO | 2012140865 A1 | 10/2012 |

OTHER PUBLICATIONS

Ermilov, et al., "Data Processing and quasi-3D optoacoustic imaging of tumors in the breast using a linear arc-shaped array of ultrasonic transducers", Proc. of SPIE, (2008), pp. 685603-1-685603-10, vol. 6856.

* cited by examiner

OBJECT INFORMATION OBTAINING DEVICE, DISPLAY METHOD, AND NON-TRANSITORY COMPUTER-READABLE STORAGE MEDIUM

CROSS-REFERENCE TO RELATED APPLICATIONS

This application is a Continuation of co-pending U.S. patent application Ser. No. 14/134,957, filed Dec. 19, 2013, which claims foreign priority benefit of Japanese Patent Application No. 2012-286685, filed Dec. 28, 2012, all of which are hereby incorporated by reference herein in their entirety.

BACKGROUND OF THE INVENTION

Field of the Invention

The present invention relates to technology to obtain object information based on a photoacoustic wave generated by irradiation of light to an object.

Description of the Related Art

Photo acoustic imaging (PAI) in an optical imaging technique developed based on the photoacoustic effect. In photo acoustic imaging, for example, an object such as a living body is irradiated with pulsed light and a light absorber such as a blood vessel absorbs energy of the pulsed light to generate a photoacoustic wave. An acoustic wave detecting unit detects the photoacoustic wave generated by the photoacoustic effect. Then, a detection signal output from the acoustic wave detecting unit is analyzed by image processing, for example, and object information is obtained.

As an example of photo acoustic imaging, Non-Patent Document 1 entitled "Universal back-projection algorithm for photoacoustic computed tomography", disclosed by Xu et al., PHYSICAL REVIEW E 71,016706 (2005), discloses obtaining initial sound pressure distribution as the object information by applying universal back-projection reconstruction processing (hereinafter, referred to as "UBP processing") to the detection signal of the photoacoustic wave.

SUMMARY OF THE INVENTION

An object information obtaining device disclosed in this specification is provided with a light source configured to emit light, an acoustic wave detecting unit configured to detect a photoacoustic wave generated by irradiation of an object with the light, and to output an electric signal in response to detection of the acoustic wave, and a processing unit configured to perform two or more types of processing to photoacoustic signal data based on the electric signal to obtain object information corresponding to each of the two or more types of processing, and to display on a display unit the object information corresponding to at least one processing selected by a user out of the two or more types of processing. Further features of the present invention will become apparent from the following description of exemplary embodiments (with reference to the attached drawings).

DESCRIPTION OF THE EMBODIMENTS

Figure 1:
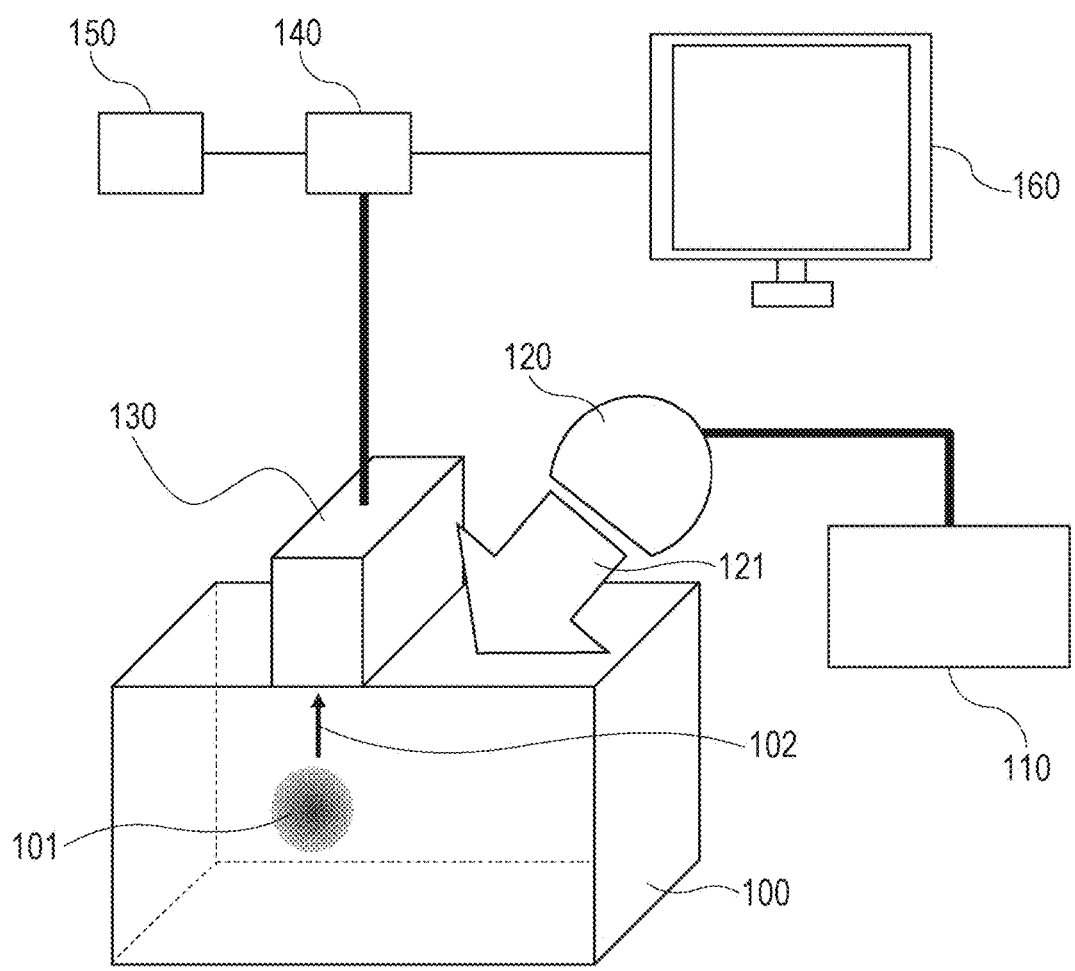
FIG. 1 is a view illustrating an object information obtaining device according to this embodiment.

Object information according to one embodiment includes initial sound pressure of a photoacoustic wave generated by a photoacoustic effect, optical energy absorption density derived from the initial sound pressure, an absorption coefficient, density of a substance forming tissue and the like. Herein, density of a substance may be determined by levels of oxygen saturation, oxyhemoglobin density, deoxyhemoglobin density, total hemoglobin density and the like. The total hemoglobin density is a sum of the oxyhemoglobin density and the deoxyhemoglobin density.

The object information in this embodiment may be not numerical data but distribution information of each position in an object. That is to say, the distribution information such as absorption coefficient distribution and oxygen saturation distribution may be used as the object information.

Further improvement in method of displaying the object information obtained only by specific processing (UBP reconstruction processing) as disclosed in Non-Patent Document 1 is desired from a diagnostic viewpoint.

For example, a real image corresponding to the object might be displayed in a different manner depending on a type of the processing. Therefore, usefulness in diagnosis of an observation object might be different depending on the type of the processing.

A virtual image referred to as an artifact might be present in a diagnostic image obtained through the reconstruction processing. The artifact might preclude appropriate diagnosis. As it is known, depending on the type of the reconstruction processing, artifacts appear differently in a reconstructed image.

Therefore, display of object information obtained by the specific processing alone might be insufficient at the time of diagnosis.

In accordance with at least one embodiment of the present invention, at least one processing is selected by a user from two or more types of processing to photoacoustic signal data (also referred to as raw data). According to this, the user may confirm the object information obtained by desired processing, so that the user may selectively use the image corresponding to the processing determined to be useful according to a symptom in the diagnosis.

With the object information obtaining device capable of executing only one specific processing, there is a case in which processing requiring long processing time should be executed even though the user wants to see a diagnostic result in a short time. With the object information obtaining device capable of executing only the specific processing, there also is a case in which processing based on a simple model should be executed even though the user wants to observe detailed information even if it takes long processing time.

Therefore, according to an embodiment disclosed herein, the user may also select the desired processing in consideration of acceptable processing time to the user. That is to say, according to this embodiment, the user may select the object information corresponding to the desired processing determined by the user to be highly useful within the acceptable processing time to the user.

The present embodiment is hereinafter described with reference to the drawings. In the drawings, the same reference sign is assigned to the same component, and the description thereof is not repeated.

A basic configuration of the object information obtaining device (information obtaining apparatus) according to this embodiment illustrated in FIG. 1 is first described.

The object information obtaining device illustrated in FIG. 1 includes a light source 110, an optical system 120, an acoustic wave detecting unit 130, a processing unit 140 as a computer, an input unit 150, and a display unit 160 in order to obtain information of a living body 100 as the object.

Figure 2:
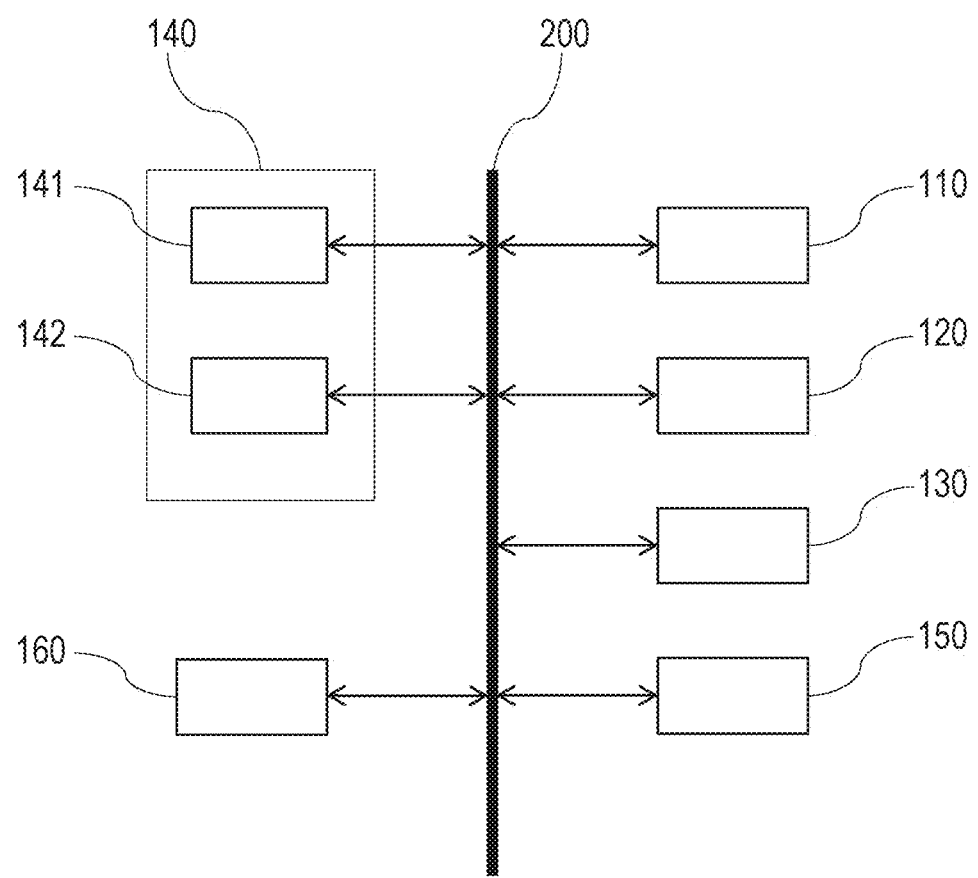
FIG. 2 is a view illustrating a processing unit according to this embodiment in detail.

FIG. 2 is a block diagram illustrating relevant parts of a computer, which is an example of a data processing apparatus including the processing unit 140 and peripheral elements of the processing unit 140. As illustrated in FIG. 2, the processing unit 140 is provided with an arithmetic unit 141 and a storage unit 142. An example of the processing unit 140 includes, but is not limited to, a microprocessor chip, such as a CPU (central processing unit) or MPU (micro processing unit). An example of storage unit 140 includes, but is not limited to, RAM or ROM memory.

The arithmetic unit 141 controls operation of each component forming the object information obtaining device through a data network 200. The arithmetic unit 141 reads a program in which processing steps for (a method of) obtaining object information to be described later is saved in the storage unit 142 and allows the object information obtaining device to execute the method of obtaining object information.

Each component of the object information obtaining device according to this embodiment is hereinafter described in detail.

(Light Source 110)

The light source 110 is preferably a pulse light source capable of emitting light pulses lasting a few nanoseconds to few microseconds. Specifically, the light source 110 is preferably capable of emitting light having a pulse width of approximately 10 nanoseconds in order to efficiently generate the photoacoustic wave. A wavelength of the light which can be emitted by the light source 110 is desirably the wavelength at which the light propagates into the object. Specifically, when the object is a living body, such as a human or animal body, a preferable wavelength is not shorter than 500 nm and not longer than 1500 nm.

A laser or a light-emitting diode are examples of a light source that may be used in some embodiments disclosed herein. As the laser, various lasers such as a solid-state laser, a gas laser, a dye laser, and a semiconductor laser may be used. For example, the laser used in this embodiment includes an alexandrite laser, an yttrium-aluminum-garnet laser, a titanium-sapphire laser and the like.

(Optical System 120)

The light emitted from the light source 110 is typically guided to the living body 100 while being shaped into a desired light distribution shape by means of an optical component such as a lens and a mirror. In addition, it is also possible to propagate the pulsed light by using a waveguide or an optical fiber. The optical component used to shape the light distribution includes, for example, a mirror reflecting the light, a lens collecting and magnifying the light or changing a focusing shape thereof, a prism dispersing, refracting, and reflecting the light, the optical fiber propagating the light, a diffusion plate dispersing the light and other like optical components or combinations thereof. Any type or number of such optical components may be used as long as the object is irradiated with the light emitted from the light source 110 in the desired manner.

However, when the light emitted by the light source 110 may be guided directly to the object as desired light, it may not be necessary to use the optical system 120.

(Acoustic Wave Detecting Unit 130)

The acoustic wave detecting unit 130 is provided with one or more opto-acoustic transducers and a housing enclosing the transducer(s). An opto-acoustic transducer, as used herein, is an element capable of detecting an acoustic wave.

The transducer receives the acoustic wave such as the photoacoustic wave and an ultrasonic echo to transform it to an electric signal being an analog signal. Any transducer may be used as long as the transducer is configured to receive the acoustic wave. Examples of transducer include a transducer using a piezoelectric phenomenon, a transducer using optical resonance, a transducer using change in capacitance, and other like transducers. The acoustic wave detecting unit 130 is preferably provided with a plurality of transducers arranged in an array.

(Processing Unit 140)

The processing unit 140 is provided with the arithmetic unit 141 and the storage unit 142 as illustrated in FIG. 2.

The arithmetic unit 141 is typically formed of an arithmetic element such as a CPU, a GPU, an A/D converter, a FPGA (field programmable gate array) card, and an ASIC (application specific integrated circuit) chip. Meanwhile, the arithmetic unit 141 may be formed not only of one arithmetic element but also of a plurality of arithmetic elements. Any arithmetic element may be used to perform the disclosed process.

The storage unit 142 is typically formed of a storage medium such as a ROM memory, a RAM memory, a hard disk drive, or a combination thereof. That is, the storage unit 142 may be formed not only of one storage medium but also of a plurality of storage media.

The arithmetic unit 141 may make a gain adjustment to increase or decrease an amplification gain according to time that elapses from irradiation of the light to arrival of the acoustic wave at the element of the acoustic wave detecting unit 130 in order to obtain the image having a uniform contrast regardless of a depth in the living body.

The arithmetic unit 141 may control light emission timing of the pulsed light emitted from the light source 110, and may also control operation start timing of the acoustic wave detecting unit 130 by using the pulsed light as a trigger signal. The arithmetic unit 141 may control display operations of the display unit 160.

The arithmetic unit 141 is preferably configured to simultaneously perform pipeline processing of a plurality of signals when a plurality of detecting signals is obtained from the acoustic wave detecting unit 130. According to this, time that elapses before the object information is obtained may be shortened.

Preferably, each processing operation performed by the processing unit 140 may be saved in the storage unit 142 as part of the program to be executed by the arithmetic unit 141. The storage unit 142 in which the program is saved is a non-transitory computer-readable recording medium.

The processing unit 140 and the acoustic wave detecting unit 130 may be provided as an integrated unit. Then, the processing unit provided on the acoustic wave detecting unit may perform a part of signal processing, and the processing unit provided outside the acoustic wave detecting unit may perform the remainder of signal processing. In this case, the processing unit provided on the acoustic wave detecting unit and the processing unit provided outside the acoustic wave detecting unit may be collectively referred to as the processing unit according to this embodiment.

(Input Unit 150)

The input unit 150 is a user interface (I/F) configured to accept an operation (e.g., input) by the user. Information input by the user is input from the input unit 150 to the processing unit 140.

For example, a pointing device such as a mouse and a keyboard, a graphics tablet type and the like may be adapted as the input unit 150. A mechanical device such as a button and a dial provided on a device forming the object information obtaining device, or other I/F device may also be adapted as the input unit 150. When a touch panel display is used as the display unit 160, the display unit 160 may also be adapted to function as the input unit 150.

Naturally, the input unit 150 may be provided as a user I/F disposed separately from the object information obtaining device and connected thereto via the data network 200.

(Display Unit 160)

The display unit 160 is a device which displays the object information output from the processing unit 140.

Although a liquid crystal display (LCD) and the like is typically used as the display unit 160, another type of display such as a plasma display, an organic EL display, and a FED may also be used. It is also possible to integrally form the input unit 150 and the display unit 160 by adopting the touch panel display as the display unit 160.

The display unit 160 may also be provided separately from the object information obtaining device according to this embodiment.

Figure 3:
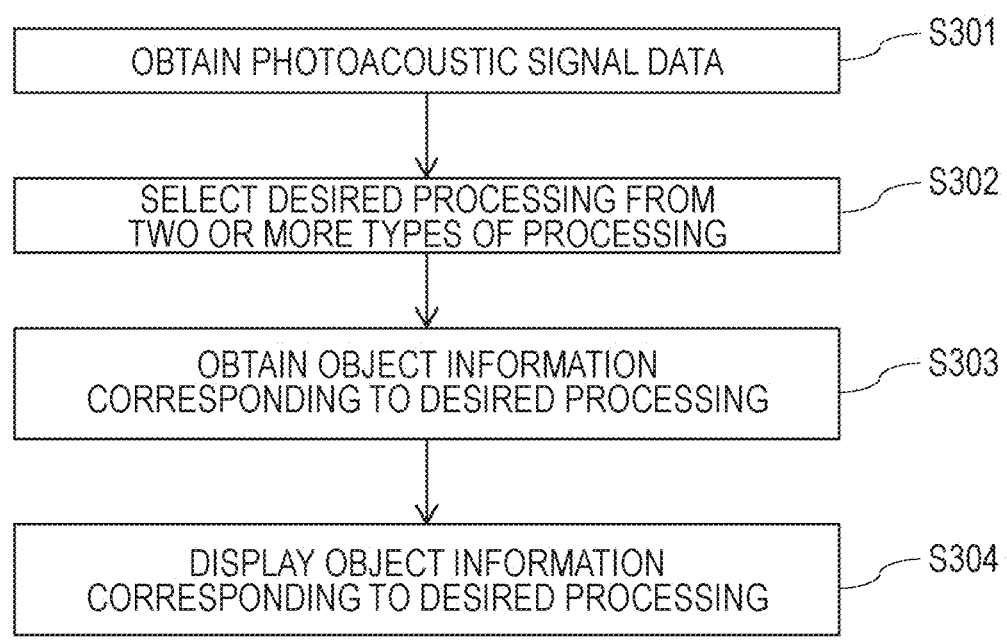
FIG. 3 is a view illustrating a flow of a method of obtaining object information according to this embodiment.

Next, the method of obtaining object information according to this embodiment using the object information obtaining device illustrated in FIGS. 1 and 2 is described with reference to a flow illustrated in FIG. 3. The flow process illustrated in FIG. 3 is example of an algorithm executed by the processing unit 140.

(S301: Step of Obtaining Photoacoustic Signal Data)

At step S301, the light emitted by the light source 110 is applied to the living body 100 as pulse light 121 through the optical system 120. Then, a light absorber 101 absorbs the pulse light 121 and a photoacoustic wave 102 is generated by the photoacoustic effect.

Next, the acoustic wave detecting unit 130 transforms the photoacoustic wave 102 to the electric signal being the analog signal to output to the processing unit 140. The arithmetic unit 141 saves the electric signal output from the acoustic wave detecting unit 130 in the storage unit 142 as the photoacoustic signal data.

In this embodiment, data obtained when the electric signal output from the acoustic wave detecting unit 130 is saved in the storage unit 142 is made into the photoacoustic signal data. The photoacoustic signal data may be read from the storage unit 142 by the arithmetic unit 141 to be used in the two or more types of processing to be described later.

The electric signal output from the acoustic wave detecting unit 130 is typically amplified and subjected to the A/D conversion to be saved in the storage unit 142 as the photoacoustic signal data. The electric signal output from the acoustic wave detecting unit 130 may also be saved in the storage unit 142 as the photoacoustic signal data after being averaged.

The photoacoustic signal data is saved in the storage unit 142 in this manner. The arithmetic unit 141 may use the photoacoustic signal data including the same photoacoustic signal data corresponding to the photoacoustic wave detected at certain time in a plurality of types of processing to be described later.

In photo acoustic imaging, it is possible to apply different types of processing to the photoacoustic signal data including the same photoacoustic signal data obtained by detecting the photoacoustic wave at certain time. According to this, the object information at the same time corresponding to each of the different types of processing may be obtained.

That is, the object information corresponding to the desired processing out of pieces of object information at the same time obtained by applying each of the two or more types of processing to the photoacoustic signal data including the same data may be selectively displayed.

The arithmetic unit 141 may also obtain the object information corresponding to each processing by performing the two or more types of processing to the photoacoustic signal data not including the same data.

(S302: Step of Selecting Information of Desired Processing from Two or More Types of Processing)

At step S302, the user selects the desired processing from two or more types of processing by using the input unit 150. Then, the input unit 150 outputs the information of the processing selected by the user to the processing unit 140. At that time, the information of the selected processing is saved in the storage unit 142.

An example of the input unit 150 for the user to select the desired processing from the two or more types of processing is hereinafter described. That is, an example of a method of inputting the information of the desired processing by the user is described.

For example, the user may select the desired processing by pressing a mechanical button as the input unit 150 corresponding to each of the two or more types of processing. Alternatively, the user may select the desired processing by turning a mechanical dial as the input unit 150 corresponding to each of the two or more types of processing.

As another example, the user may also select the desired processing by selecting an item indicating the processing displayed on the display unit 160 by means of a pointing device (mouse), the keyboard and the like as the input unit 150. At that time, the display unit 160 may display the items indicating the processing next to one another as icons or display them as a menu. The item related to the processing displayed on the display unit 160 may be always displayed beside the image of the object information or may be configured to be displayed when the user performs some operation by using the input unit 150. For example, the display unit 160 may be configured such that the item indicating the processing is displayed on the display unit 160 by a click of the mechanical button provided on the mouse as the input unit 150.

The method is not limited to the above-described method and any method may be adopted as long as the user may select the desired processing out of the two or more types of processing.

The object information obtaining device is preferably configured such that progress of each processing is visually presented to the user. For example, it is possible to configure the object information obtaining device such that the progress of each processing is visually presented by displaying a progress bar or displaying a predicted calculation termination time on the display unit 160. In addition, it is also possible to use a circular progress mark in which an angle of a part with changed color changes as the processing advances. Alternatively, a color of the item corresponding to the processing may be changed according to a progress status such as completion of the processing or the progress status may be displayed in characters in the vicinity of the item.

The object information obtaining device according to this embodiment is preferably configured such that the progress of the processing may be grasped and the user may optionally stop the processing currently being calculated. Such configuration allows the user to start a different process operation when the user sees the progress bar and determines that the progress of the processing currently being calculated is not convenient (e.g., the processing is taking too long, the processing is not good due to a processing error, the type of processing was chosen in error, etc.).

Image reconstruction processing selected by default may be set in advance in a file in the storage unit 142. In this case, the arithmetic unit 141 may read default processing at the beginning of step S302 and execute the processing selected by default if the user does not especially select other processing. It is also possible that the user may intentionally select the processing set by default.

The desired processing selected by the user may be at least one type of processing. In this embodiment, at least two types of processing may be selected from three or more types of processing. At that time, the object information obtaining device according to this embodiment may be configured such that a plurality of combinations of at least two types of processing may be selected. According to this, the user may select the desired processing with a high degree of freedom and it becomes possible to display the object information useful in the diagnosis.

(S303: Step of Obtaining Object Information by Performing Desired Processing)

At step S303, the arithmetic unit 141 obtains the object information by performing the desired processing selected at S200 based on the photoacoustic signal data saved in the storage unit 142. Herein, the object information obtained by performing the desired processing is referred to as "object information corresponding to the desired processing".

Meanwhile, the arithmetic unit 141 may read the program in which an algorithm of the processing is described stored in the storage unit 142 and apply this processing to the photoacoustic signal data to obtain the object information.

In this embodiment, three-dimensional voxel data and two-dimensional pixel data as the object information may be obtained by the processing.

Herein, the processing according to this embodiment is intended to mean every processing performed during transform from the photoacoustic signal data to the object information having a pathological value. For example, the processing according to this embodiment includes signal processing such as probe response correction processing and noise removal processing to generate different photoacoustic signal data based on the photoacoustic signal data stored in the storage unit 142. There also is, for example, reconstruction processing such as time domain reconstruction processing, Fourier domain reconstruction processing, and model base reconstruction processing to generate the object information from the photoacoustic signal data stored in the storage unit 142 as the processing according to this embodiment. For example, the processing according to this embodiment includes image processing such as resolution improvement processing to generate different object information based on the object information generated by the above-described reconstruction processing.

An example of each processing is hereinafter described.

The probe response correction processing (hereinafter, referred to as "BD processing") as the signal processing according to this embodiment is the processing to correct signal deterioration due to band limitation of a probe by applying processing based on a blind deconvolution algorithm to the photoacoustic signal data (refer to Patent Document 1 (Japanese Patent Application Laid-Open No. 2012-135462)). When the photoacoustic wave is transformed to the electric signal by the acoustic wave detecting unit 130, there is limitation in receiving bandwidth of the acoustic wave detecting unit 130, so that a waveform of the electric signal might change to generate ringing. This ringing causes the artifact appearing in the vicinity of the light absorber on the image to deteriorate resolution. Probe response correction has an effect of decreasing the ringing by the acoustic wave detecting unit, thereby decreasing the artifact and improving the resolution.

The noise removal processing (hereinafter, referred to as "wavelet processing") as the signal processing according to this embodiment is the processing to remove a noise component of the photoacoustic signal data through basis pursuit by a wavelet function of the photoacoustic signal data. A waveform of the signal resulting from the photoacoustic wave is known to be an N-shaped waveform under an ideal condition (refer to Non-Patent Document 2 (Sergey A. Ermilov, RedaGharieb, Andre Conjusteau, Tom Miller, Ketan Mehta, and Alexander A. Oraevsky, "Data Processing and quasi-3D optoacoustic imaging of tumors in the breast using a linear arc-shaped array of ultrasonic transducers", Proc. of SPIE, Vol. 6856). On the other hand, random noise being an irregular waveform mixed from an electric system and the like of the device is superimposed on the signal resulting from the photoacoustic wave. Therefore, the signal resulting from the noise is discriminated from the signal resulting from the photoacoustic wave by applying a discrete wavelet transform to the photoacoustic signal data and removing a coefficient having a small absolute value from a result thereof. The wavelet processing has a large effect when the signal resulting from the photo acoustic wave has the waveform close to the ideal waveform. On the other hand, when a frequency of the photoacoustic wave is significantly different from a bandwidth of the acoustic wave detecting unit, when the noise is too large, and when a plurality of waveforms are superimposed due to a feature of the object, there is a case in which an effect of improving an image quality by the wavelet processing is small.

The time domain reconstruction processing (hereinafter, referred to as "TD processing") as the reconstruction processing is the processing to estimate a sonic wave source by superimposing sonic wave signals in a real space by using a property that the photoacoustic wave is a spherical wave to generate the voxel data (refer to Patent Document 2 (Japanese Patent Application Laid-Open No. 2010-35806)). The TD processing specifically includes UBP processing disclosed in Non-Patent Document 1. The TD processing is performed in the real space, so that an effect of a measurement system is easily introduced as compared to the Fourier domain reconstruction processing and the like to be described later. For example, it is possible to decrease a side-lobe artifact by applying weighted correction processing of a solid angle and the like in consideration of a state of the acoustic wave detecting unit 130, for example.

The Fourier domain reconstruction processing (hereinafter, referred to as "FD processing") as the reconstruction processing is the processing to estimate the sonic wave source by superimposing the detection signals in a frequency domain by using a Fourier transform and an inverse Fourier transform to generate the voxel data (refer to Japanese Patent Application Laid-Open No. 2010-35806). The processing may be performed in a short time by using a fast Fourier transform. However, the effect of the measurement system is not easily introduced in a frequency space as compared to the real space. Therefore, it is difficult to apply the weighted correction processing of the solid angle and the like in consideration of the state of the acoustic wave detecting unit which may be performed in the TD processing, for example, and there is a case in which the side-lobe artifact is generated.

The model base reconstruction processing (hereinafter, referred to as "MBP processing") as the reconstruction processing is the processing to estimate the sonic wave source such that difference between a calculation result based on a propagation model of an ideal photoacoustic wave and the photoacoustic signal data is minimum to generate the voxel data (refer to Patent Document 3 (Japanese Patent Application Laid-Open No. 2011-143175)). By using a descriptive model of a phenomenon, the measurement system may be more strictly described than in the TD processing and the FD processing. According to this, an image with few artifacts may be obtained. However, since it is required to repetitively calculate such that the difference between the photoacoustic signal data and the calculation result is minimum in the MBP processing, longer processing time than that in the TD processing and the FD processing is typically required. It is difficult to reflect all the phenomena in the model, and when a generated phenomenon cannot be reflected in the model, there is a case in which quantitativeness of the object information obtained by the MBP processing is deteriorated.

The resolution improvement processing (hereinafter, referred to as "CF processing") as the image processing is the processing to reduce the artifact generated by limitation of a viewing angle of the probe by using a coherent filter in the object information obtained by the above-described reconstruction processing (refer to Patent Document 4 (Japanese Patent Application Laid-Open No. 2011-120765). According to this, a high-resolution image of the object information may be obtained. This is the processing to calculate a coefficient which is set to 1 when phase signals of the photoacoustic wave are in phase and set to 0 when they are out of phase for each voxel and multiply distribution of the coefficients by the image. The CF processing is especially effective when sound speed distribution of the object is nearly constant. On the other hand, when variation in the sound speed distribution of the object is large, an effect of improving the image quality by the CF processing might be small.

Figure 4B:
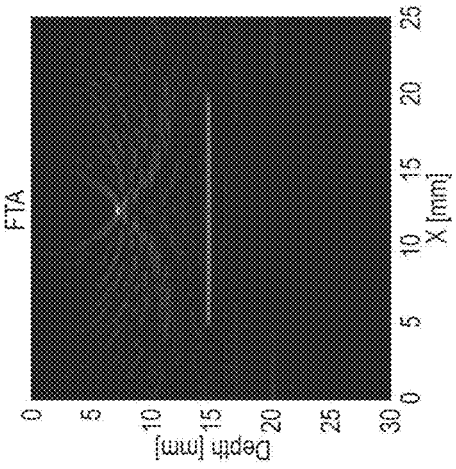
FIG. 4B is a view illustrating a simulation result of a Fourier domain reconstruction processing according to this embodiment.
Figure 4D:
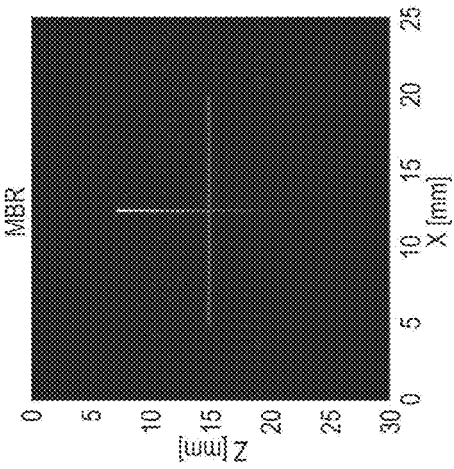
FIG. 4D is a view illustrating a simulation result of a model base reconstruction processing according to this embodiment.
Figure 4A:
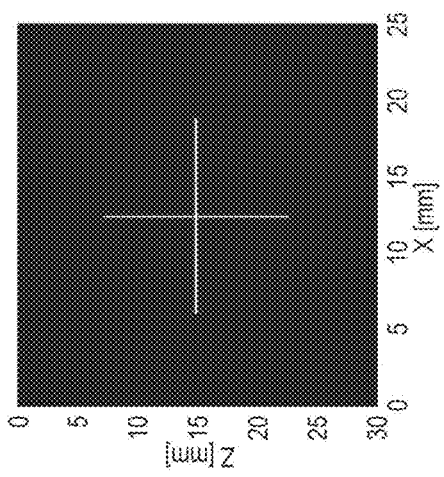
FIG. 4A is a view illustrating a simulation model according to this embodiment.

Hereinafter, a result obtained when various types of reconstruction processing are applied to the photoacoustic signal data obtained by simulating step S301 using a model having absorption coefficient distribution illustrated in FIG. 4A is described. Herein, an x-axis corresponds to a horizontal direction and a z-axis corresponds to a vertical direction in FIG. 4A. Herein, a case in which a one-dimensional transducer array in an x-axis direction is arranged on a lowest part in FIG. 4A and the one-dimensional transducer array detects the photoacoustic wave propagated from an upper side of the z-axis is simulated.

Figure 4C:
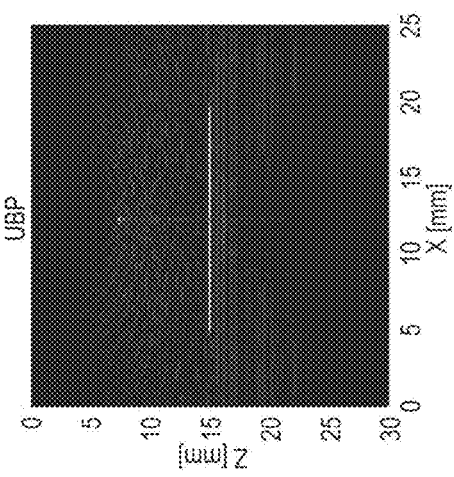
FIG. 4C is a view illustrating a simulation result of a time domain reconstruction processing according to this embodiment.

FIG. 4B illustrates initial sound pressure distribution when the FD processing is performed. FIG. 4C illustrates the initial sound pressure distribution when the TD processing is performed. FIG. 4D illustrates the initial sound pressure distribution when the MBP processing is performed.

As is understood from the images in FIGS. 4B to 4D, different images are obtained for the same absorption coefficient distribution depending on the type of the processing.

For example, in the image obtained by the FD processing illustrated in FIG. 4B, an arc-like artifact is confirmed. In the image obtained by the TD processing illustrated in FIG. 4C, the artifact extending in the x-axis direction is confirmed. It is understood that the artifact in the image obtained by the MBP processing illustrated in FIG. 4D is entirely suppressed as compared to the artifact in the images illustrated in FIGS. 4B and 4C.

In the images illustrated in FIGS. 4B and 4C, it is understood that connection of the initial sound pressure distribution corresponding to the absorption coefficient distribution extending in a z-axis direction decreases as compared to that in the image illustrated in FIG. 4D.

As described above, appropriate processing differs according to a measurement environment and a site wanted to be observed. Time required for the processing differs depending on the type of processing.

(S304: Step of Displaying Object Information Corresponding to Desired Processing)

At this step, the arithmetic unit 141 calculates display data to be displayed on the display unit 160 based on the voxel data (or the pixel data) of the object information saved in the storage unit 142 to display the display data on the display unit 160.

Meanwhile, the display data of desired dimension out of one dimension, two dimensions, and three dimensions may be obtained from the voxel data (or the pixel data). The object information obtaining device may be configured such that the user may set the dimension of the display data by using the input unit 150.

As described above, in the object information obtaining device according to this embodiment, it is possible to display the object information corresponding to the desired processing selected by the user out of the two or more types of processing on the display unit. According to this, it is possible to diagnose by using the image meeting needs of the user such as the processing time and the image quality from the images at the same time obtained by each image reconstruction.

The configuration in which the object information corresponding to the desired processing is obtained after the information of the desired processing is obtained is described above. However, the object information obtaining device according to this embodiment may also be configured such that the information of the desired processing is obtained and the object information corresponding to the information of the desired processing is displayed in a state in which the object information corresponding to the desired processing is obtained in advance. That is to say, step S302 may be executed after step S303 is executed and step S304 may be executed thereafter.

In this case, the image itself obtained after the processing is applied to the photoacoustic signal data may be adopted as the item indicating the processing. That is to say, the user may select the processing by selecting the image. For example, it is possible that the images whose processing is finished are sequentially displayed on the display unit 160 and when the user selects one of a plurality of images, the image is displayed in an enlarged manner. By this method, the user may compare results of a plurality of types of processing and may select the desired image even when the user does not have knowledge of the processing.

In this case, the object information obtaining device is preferably configured such that the user cannot select the processing not finished yet.

In this case, the object information obtaining device is preferably further provided with notifying means of notifying the user of whether the processing is finished processing. Further, the notifying means is preferably configured such that the user may visually recognize whether the processing is the finished processing.

For example, when the item indicating the object information is displayed on the display unit 160, it is possible to display the item of the finished processing and the item of the processing not finished yet in different colors and the like as the notifying means.

It is also possible to provide a lamp as the notifying means corresponding to each processing on the device forming the object information obtaining device or another device. In this case, it is possible to notify the user of whether the processing is the finished processing by setting such that the lamp corresponding the finished processing is turned on, for example.

It is also possible that the information of the desired processing is obtained and the object information corresponding to the desired processing is displayed on the display unit 160 in a state in which the object information different from the object information corresponding to the desired processing is displayed on the display unit 160. At that time, the object information corresponding to the desired processing may be displayed so as to be superimposed on the object information displayed in advance or may be displayed next to the same. It is also possible to switch from the object information displayed in advance to the object information corresponding to the desired processing to display on the display unit 160. That is to say, it is possible to hide the object information displayed in advance from the display unit 160 and display the object information corresponding to the desired processing in an area on the display unit 160 in which the object information is displayed. The display method may be set in advance before shipping or may be set by the user by means of the input unit 150.

In this manner, the user may grasp pathological information which may be grasped from the object information displayed in advance and the pathological information which may grasped from the object information corresponding to the desired processing to diagnose in a comprehensive manner. It is also possible to diagnose in a comprehensive manner by grasping a plurality of pieces of pathological information without a time interval.

[Example 1]

Figure 5:
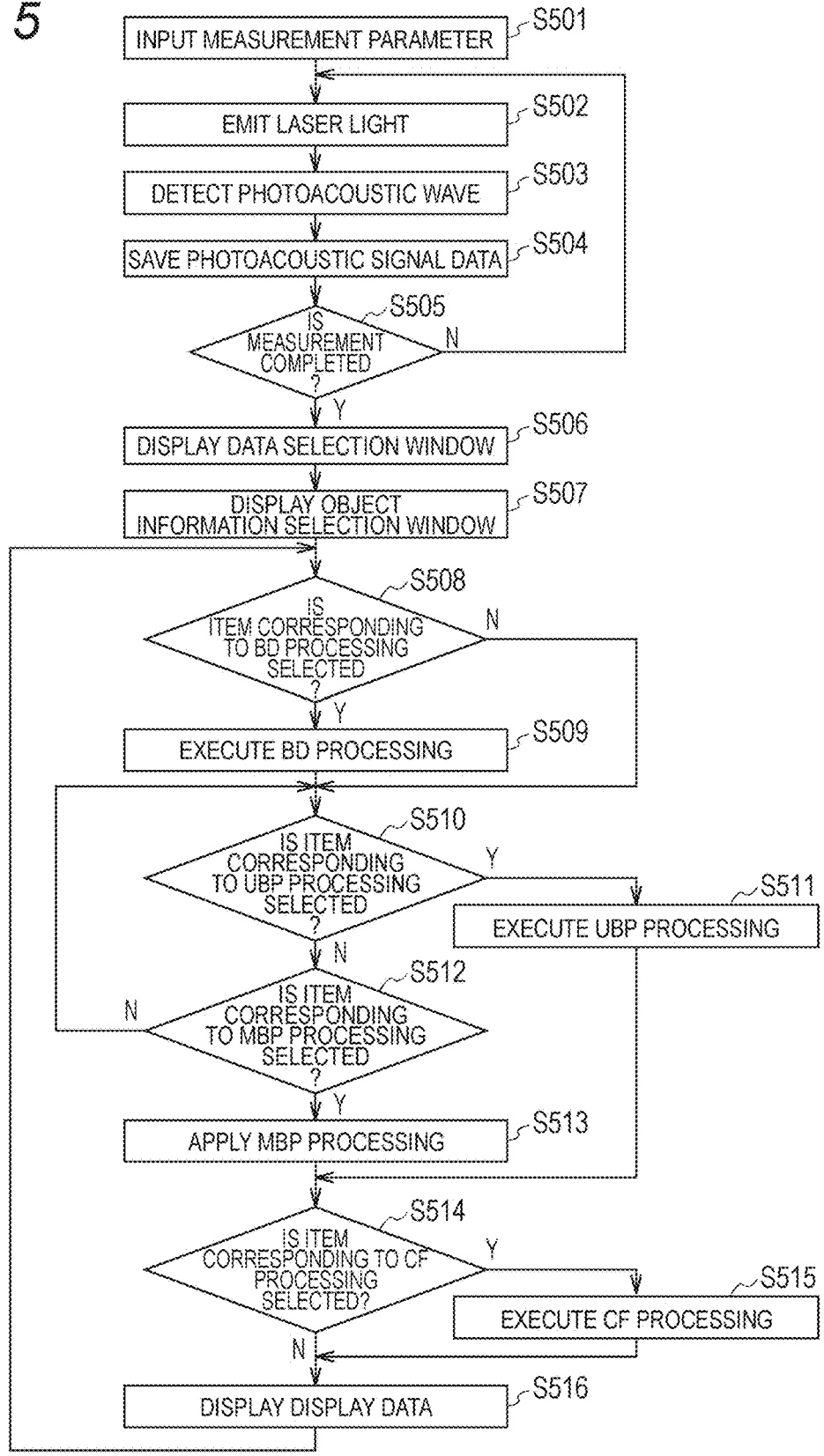
FIG. 5 is a view illustrating a flow of a method of obtaining object information according to Example 1 of the present invention.
Figure 6:
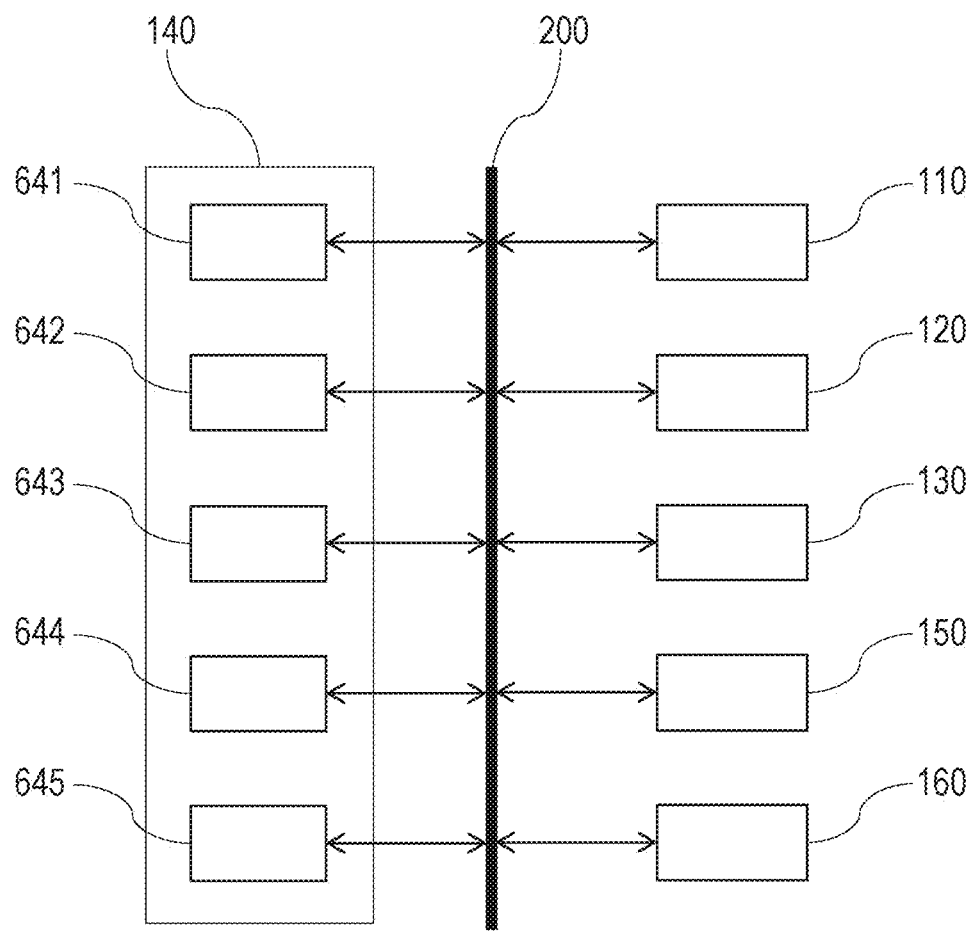
FIG. 6 is a view illustrating a processing unit according to Example 1 of the present invention in detail.

Example 1 according to the present invention is subsequently described with reference to FIGS. 1, 5, and 6. FIG. 5 is a flow diagram of a method of obtaining object information according to this example. FIG. 6 is a schematic diagram illustrating a computer 140 as a processing unit according to this example in detail and a peripheral device. As illustrated in FIG. 6, the computer 140 is provided with a CPU 641, a FPGA 642, and a GPU 643 as an arithmetic unit, and a ROM 644 and a RAM 645 as a storage unit. Herein, the ROM 644 is used as a non-transitory computer-readable recording medium.

In this example, the CPU 641 controls operation of each component forming an object information obtaining device through a data network 200, which is similar to that shown in FIG. 2. The CPU 641 reads a program in which the method of obtaining object information according to this example is described saved in the ROM 644 to allow the object information obtaining device to execute the method of obtaining object information. That is to say, the computer 140 executes a flow illustrated in FIG. 5.

At step S501, a user operated an input unit 150 to input a measurement parameter. The measurement parameter was saved in the RAM 645 as the storage unit. At this step, the user set a wavelength of laser light used in measurement and the number of irradiation times of the laser light to a breast 100 of a subject as an object in one measurement as the measurement parameters. Meanwhile, in this example, the user set the wavelength of the laser light used in the measurement to 797 nm and the number of irradiation times of the laser light to 30.

Subsequently, at step S502, the CPU 641 issues an instruction based on the measurement parameter to a titanium-sapphire laser 110 as a light source to allow the same to emit the laser light. The laser light was applied to the breast 100 as pulse light 121 with a pulse width of 50 nm through an optical fiber 120. Then, the breast 100 absorbed the pulse light 121 and a photoacoustic wave reflecting absorption coefficient distribution in the breast 100 was generated. Meanwhile, the titan-sapphire laser 110 in this example includes a flash lamp and a Q-switch as means of exciting an internal laser medium and light emission timing was controlled by the instruction from the CPU 641.

Subsequently, at step S503, a CMUT array 130 as an acoustic wave detecting unit transformed the photoacoustic wave to an electric signal and output the electric signal to the processing unit 140.

Meanwhile, the CPU 641 instructs the CMUT array 130 to detect the photoacoustic wave in synchronization with the instruction to emit the laser light at step S502. In this example, ultrasonic gel whose acoustic impedance is close to that of the breast 100 was provided as an acoustic matching medium between the CMUT array 130 and the breast 100.

Subsequently, at step S504, the FPGA 642 amplified the electric signal and performed A/D conversion thereof. The CPU 641 saved the signal amplified and subjected to the A/D conversion in the RAM 645 as photoacoustic signal data.

Subsequently, at step S505, it was determined whether the measurement of the object was completed. When the measurement of the object is completed, the procedure shifts to step S506. When the measurement of the object is not completed, the procedure shifts to step S502. In this example, since the number of irradiation times of the laser light was set to 30 at step S501, the measurement is completed when the procedure from step S502 to step S504 is repeated 30 times.

Figure 7:
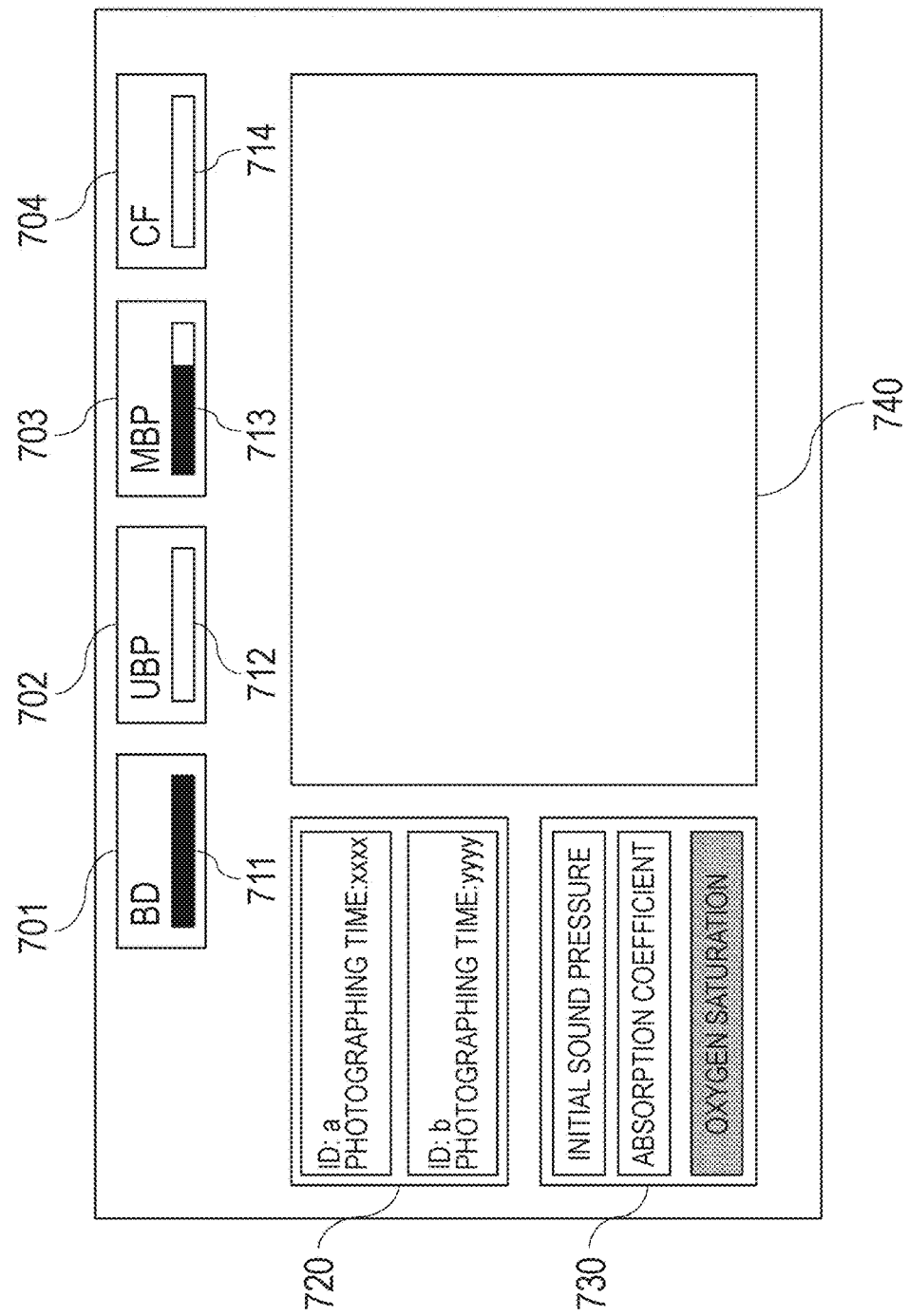
FIG. 7 is a view illustrating a screen displayed on a display according to Example 1 of the present invention.

A screen displayed on a liquid crystal display 160 as a display unit used in a following step is illustrated in FIG. 7. The user may select a desired item from an item 701 corresponding to BD processing, an item 702 corresponding to UBP processing, an item 703 corresponding to MBP processing, and an item 704 corresponding to CF processing.

The items 701 to 704 corresponding to each processing and progress bars 711 to 714 indicating a progress situation of each processing are displayed next to one another. When a black bar of each of the progress bars 711 to 714 is located on a left end, progress of the corresponding processing is indicated to be 0% and when this reaches a right end, the progress of the corresponding processing is indicated to be 100%. By this configuration, the user may grasp the progress situation and time remained of the corresponding processing from a position and a speed of the progress bar.

FIG. 7 illustrates the screen displayed when the item 701 corresponding to the BD processing is selected at step S508 to be described later and the item 703 corresponding to the MBP processing is selected at step S512 thereafter. At that time, the black bar of the progress bar 713 corresponding the MBP processing does not reach the right end as illustrated in FIG. 7. Therefore, it is understood that the MBP processing is not finished at that time.

Subsequently, at step S506, the CPU 641 referred to the RAM 645 and displayed a list of pieces of the saved photoacoustic signal data in a data selection window 720. Then, the user selected one of the pieces of photoacoustic signal data displayed in the data selection window 720.

Meanwhile, in this example, an ID number of the subject and photographing time of the photoacoustic signal data are displayed in the data selection window 720 such that they may be selected.

Subsequently, at step S507, the CPU 641 read the measurement parameter corresponding to the photoacoustic signal data selected by the user at step S506 and displayed the object information which may be displayed in an object information selection window 730. Then, the user selected the item corresponding to initial sound pressure.

The initial sound pressure, an absorption coefficient, and oxygen saturation are displayed in the object information selection window 730. However, since it was measured by using only one wavelength 797 nm, the oxygen saturation being spectral characteristics cannot be selected in this example. The initial sound pressure and the absorption coefficient which may be selected by the user and the oxygen saturation which cannot be selected by the user are displayed in different colors.

Subsequently, at step S508, the CPU 641 determines whether the item 701 corresponding to the BD processing is selected by the user. When the item 701 corresponding to the BD processing is selected, the procedure shifts to step S509. When the item 701 corresponding to the BD processing is not selected, the procedure shifts to step S510. Meanwhile, since the user selects the item 701 corresponding to the BD processing, the procedure shifts to step S509 in this example.

Subsequently, at step S509, the CPU 641 read the photoacoustic signal data selected by the user from the RAM 645 and applied the above-described BD processing to the photoacoustic signal data. Then, the photoacoustic signal data to which the BD processing was applied was saved in the RAM 645.

Subsequently, at step S510, the CPU 641 determined whether the item 702 corresponding to the UBP processing was selected. When the item 702 corresponding to the UBP processing is selected, the procedure shifts to step S511. When the item 702 corresponding to the UBP processing is not selected, the procedure shifts to step S512. Since the user does not select the item 702 corresponding to the UBP processing, the procedure shifts to step S512 in this example.

Subsequently, at step S512, the CPU 641 determined whether the item 703 corresponding to the MBP processing was selected. When the item 703 corresponding to the MBP processing is selected, the procedure shifts to step S513. When the item 703 corresponding to the MBP processing is not selected, the procedure shifts to step S510. Meanwhile, since the user selects the item 703 corresponding to the MBP processing, the procedure shifts to S513 in this example.

Subsequently, at step S513, the CPU 641 instructed the GPU 643 to perform the MBP processing. Then, the GPU 643 applied the MBP processing to the photoacoustic signal data to which the BD processing was applied at step S509 to generate three-dimensional voxel data related to the initial sound pressure. The three-dimensional voxel data was saved in the RAM 645.

Subsequently, at step S514, the CPU 641 determines whether the item 704 corresponding to the CF processing is selected. When the item 704 corresponding to the CF processing is selected, the procedure shifts to step S515. When the item 704 corresponding to the CF processing is not selected, the procedure shifts to step S516. In this example, the user selects the item 704 corresponding to the CF processing, so that the procedure shifts to step S515.

Subsequently, at step S515, the CPU 641 applied the CF processing to the three-dimensional voxel data related to the initial sound pressure stored in the RAM 645 to generate the three-dimensional voxel data related to the initial sound pressure subjected to the CF processing. Then, the three-dimensional voxel data related to the initial sound pressure after being subjected to the CF processing was saved in the RAM 645. By applying the CF processing at this step, resolution of the three-dimensional voxel data related to the initial sound pressure was improved.

Subsequently, at step S516, the GPU 643 applied scan transform processing to the three-dimensional voxel data related to the initial sound pressure stored in the RAM 645 to generate display data. Then, the CPU 641 output the display data to the liquid crystal display 160 and initial sound pressure distribution was displayed in an image display window 740.

Subsequently, the procedure shifts to step S508 again to determine whether the item corresponding to each processing is selected and when any item is selected, the processing corresponding to the item is executed.

According to this example, the user may execute the desired processing to display the object information. Therefore, the user may diagnose by using an image obtained by the processing meeting needs of the user such as processing time and an image quality by using the photoacoustic signal data obtained at certain time.

[Example 2]

Subsequently, Example 2 of the present invention is described. This example is different from Example 1 in that a plurality of types of processing is started in parallel and desired processing may be selected from finished processing.

Figure 8:
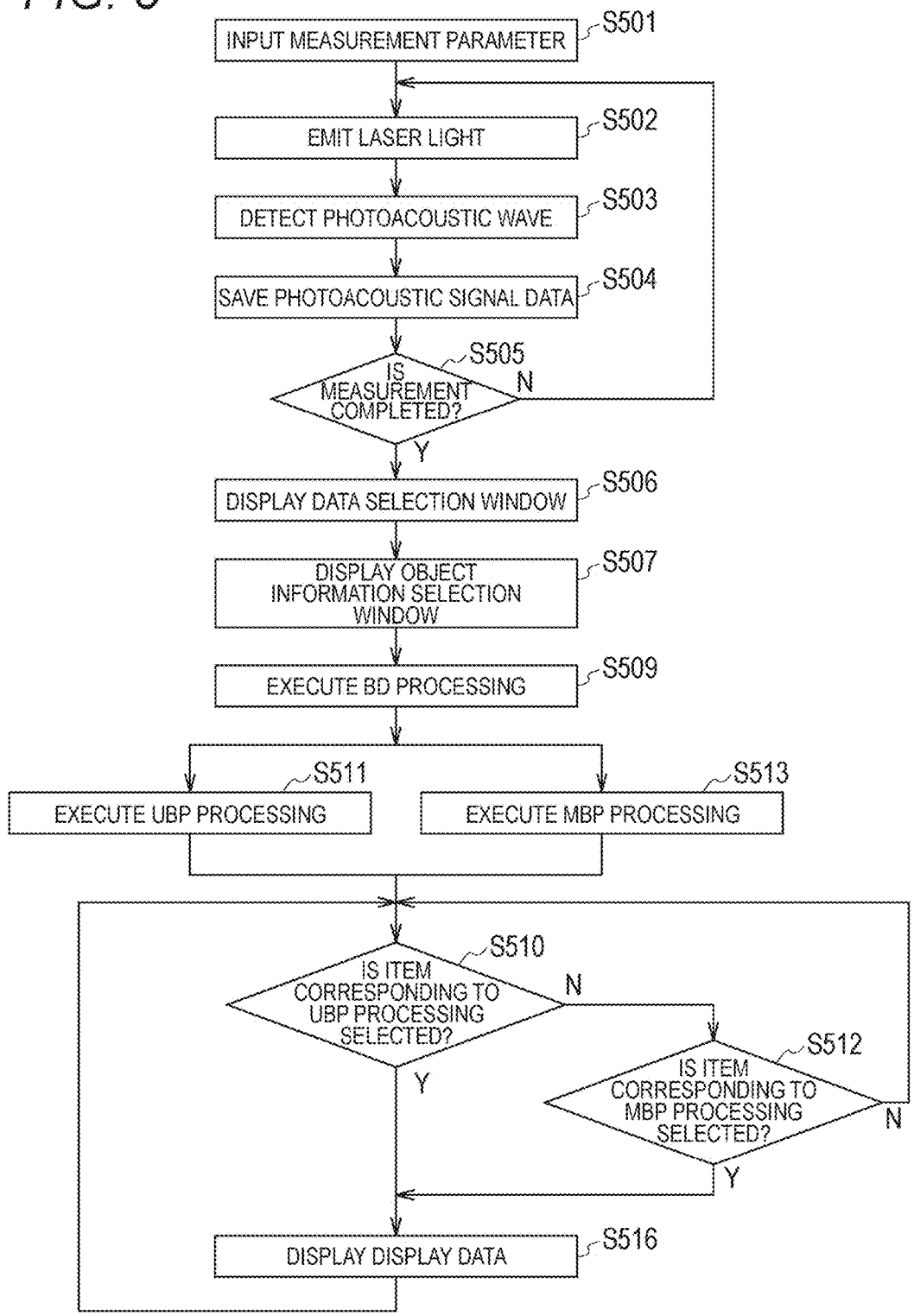
FIG. 8 is a view illustrating a flow of a method of obtaining object information according to Example 2 of the present invention.

In this example, an object information obtaining device illustrated in FIGS. 1 and 6 was used as in Example 1. Hereinafter, a method of obtaining object information of this example is described with reference to a flow illustrated in FIG. 8. Meanwhile, the flow illustrated in FIG. 8 is executed by a computer 140.

In this example, a CPU 641 issued an instruction to a GPU 643 to execute UBP processing at step S511 to photoacoustic signal data to which BD processing was applied after steps up to step S509. Further, the CPU 641 issued an instruction to the GPU 643 to execute MBP processing at step S513 in parallel with step S511.

Meanwhile, reconstruction processing is stored in a ROM 644 as a different thread program. Each processing is executed by each of a plurality of processors assigned in the GPU 643.

Figure 9:
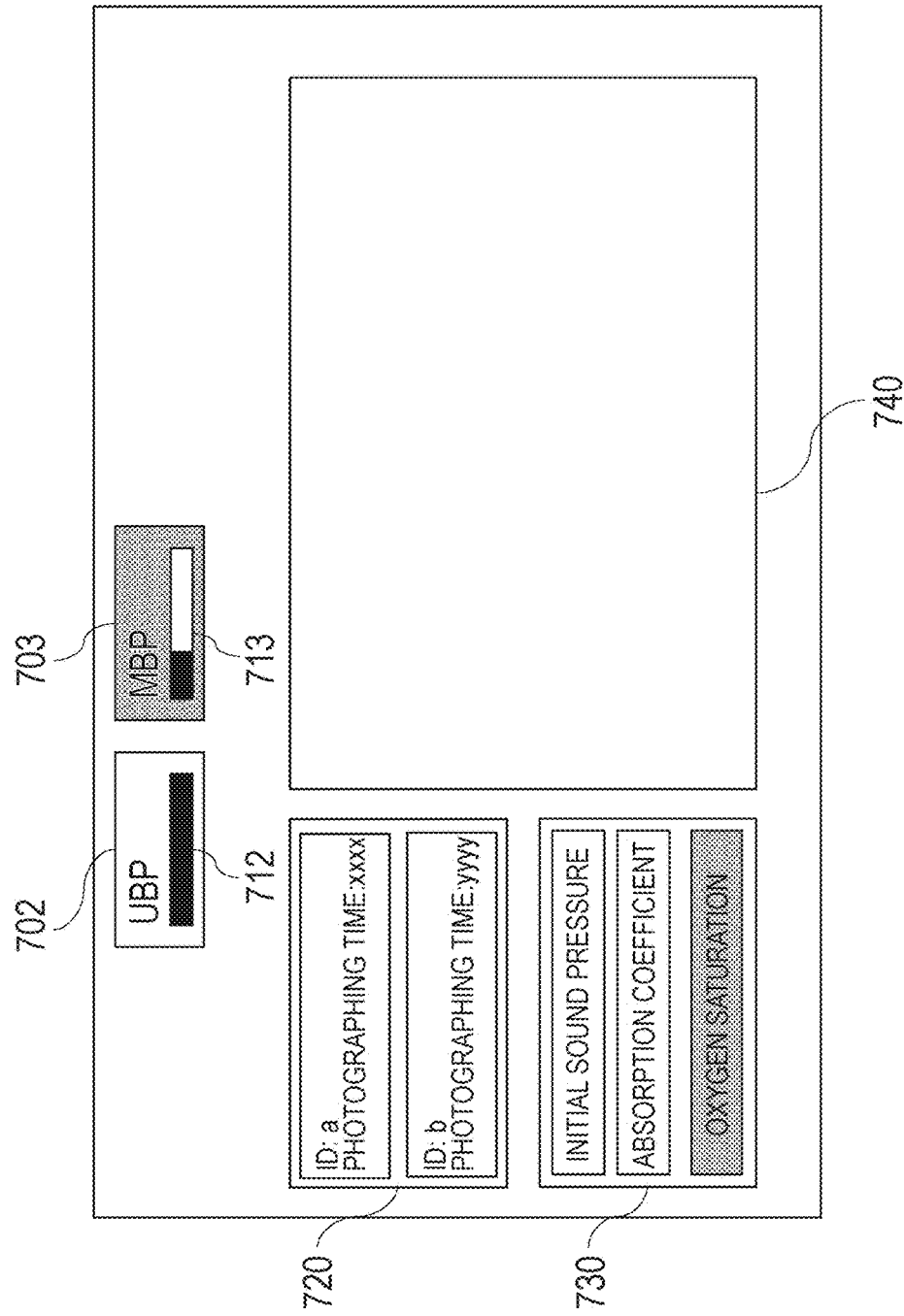
FIG. 9 is a view illustrating a screen displayed on a display according to Example 2 of the present invention.

A screen displayed on a liquid crystal display 160 at that time is illustrated in FIG. 9. When a progress bar 712 indicating progress of the UBP processing is confirmed, the progress is indicated to be 100%, so that initial sound pressure distribution corresponding to the UBP processing may be selected.

On the other hand, when a progress bar 713 indicating the progress of the MBP processing is confirmed, the progress is not indicated to be 100%. Therefore, a user cannot select an item 703 corresponding to the MBP processing. This is because the MBP processing requires longer processing time than that of the UBP processing.

In this example, an item 702 corresponding to the UBP processing which may be selected is displayed with white background and the item 703 corresponding to the MBP processing which cannot be selected is displayed with gray background, so that the user could visually recognize whether the processing may be selected.

Subsequently, at step S510, the CPU 641 determined whether the item 702 corresponding to the UBP processing was selected. When the item 702 corresponding to the UBP processing is selected, the procedure shifts to step S516. When the item 702 corresponding to the UBP processing is not selected, the procedure shifts to step S512. In this example, the user selects the item 702 corresponding to the UBP processing which previously becomes selectable, so that the procedure shifts to step S516.

Subsequently, the procedure shifts to step S510 again to determine whether the item corresponding to each processing is selected, and when any item is selected, the object information corresponding to the item is displayed.

As described above, the number of finished processing increases with time, so that the types of processing which the user may select also increase with time in this example. Therefore, a diagnostic method of confirming the object information obtained in a short time by the UBP processing and the like first and confirming the object information obtained by the MBP processing and the like when further detail is required during reading as in this example becomes possible.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processing units. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. An image generating apparatus, comprising:
a light source configured to emit light;
an acoustic wave detecting unit configured to detect a photoacoustic wave generated in an object in response to irradiation with the light and output an electric signal in response to detection of the acoustic wave; and
an arithmetic unit configured to generate photoacoustic signal data based on the electric signal and generate image data based on the photoacoustic signal data,
wherein the arithmetic unit is configured to:
cause a display unit to display a plurality of candidates in image reconstruction processing, those of which are ready to be specified by a user,
perform image reconstruction processing specified by the user on the photoacoustic signal data configured to generate the image data; and
cause the display unit to display an image based on the image data,
wherein the arithmetic unit is configured to cause the display unit to display a plurality of candidates in image reconstruction processing including a time-domain image reconstruction processing, a Fourier-domain image reconstruction processing and a model base image reconstruction processing, those of which are ready to be specified by a user, and to display a state of progress in the corresponding image reconstruction processing.

2. The image generating apparatus according to claim 1, wherein
the plurality of candidates includes time-domain image reconstruction processing, Fourier-domain image reconstruction processing and
model base image reconstruction processing.

3. The image generating apparatus according to claim 2, wherein a processing time of the time-domain image reconstruction processing is shorter than a processing time of the model base image reconstruction processing, and
wherein a processing time of the Fourier-domain image reconstruction processing is shorter than a processing time of the model base image reconstruction processing.

4. The image generating apparatus according to claim 1, further comprising a storage unit configured to store the photoacoustic signal data,
wherein the arithmetic unit is configured to generate the image data based on the photoacoustic signal data stored in the storage unit.

5. The image generating apparatus according to claim 1, wherein, in a case where none of candidates in image reconstruction processing is specified by the user, the arithmetic unit is configured to generate default image data by performing default image reconstruction processing on the photoacoustic signal data, and cause the display unit to display a default image based on the default image data.

6. The image generating apparatus according to claim 5, wherein the arithmetic unit is configured to perform,
before the image reconstruction processing is specified by the user, a provisional image reconstruction processing on the photoacoustic signal data, and
wherein, when the provisional image reconstruction processing is in association with the image reconstruction processing specified by the user after the provisional image reconstruction processing is completed, the arithmetic unit is configured to cause the display unit to display an image based on an image data obtained by the provisional image reconstruction processing instead of displaying the default image.

7. The image generating apparatus according to claim 5, wherein a processing period of time of the default image reconstruction processing is shorter than a processing period of time of the provisional image reconstruction processing.

8. The image generating apparatus according to claim 5, wherein
the default image reconstruction is time-domain image reconstruction processing or Fourier-domain image reconstruction processing,
the provisional image reconstruction is model base image reconstruction processing,
wherein a processing time of the time-domain image reconstruction processing is shorter than a processing time of the model base image reconstruction processing, and
wherein a processing time of the Fourier-domain image reconstruction processing is shorter than a processing time of the model base image reconstruction processing.

9. The image generating apparatus according to claim 8, wherein the arithmetic unit is configured to perform,
before the provisional image reconstruction processing is specified by the user, the provisional image reconstruction processing on the photoacoustic signal data, and
wherein, when the provisional image reconstruction processing is specified by the user after the provisional image reconstruction processing is completed, the arithmetic unit is configured to cause the display unit to display the image based on the image data instead of displaying the default image.

10. The image generating apparatus according to claim 1, wherein the arithmetic unit is configured to cause the display unit to display items for specifying a certain image reconstruction processing among the plurality of candidates in image reconstruction processing.

11. The image generating apparatus according to claim 10, wherein the arithmetic unit is configured to cause the display unit to display an item corresponding to image reconstruction processing which is completed and an item corresponding to image reconstruction processing which is not completed, with a different color from each other.

12. The image generating apparatus according to claim 1, wherein the arithmetic unit is configured to cause the display unit to display information which represents each progress of the default and provisional image reconstruction processing.

13. The image generating apparatus according to claim 1, wherein the arithmetic unit is configured to cause the display unit to display information which represents each predicted calculation termination time of the plurality of candidates in image reconstruction processing.

14. The image generating apparatus according to claim 1, wherein the arithmetic unit is configured to generate the image data on any one of an initial sound pressure distribution, an optical energy absorption density distribution, an absorption coefficient distribution, an oxygen saturation distribution, an oxy-hemoglobin density distribution, a deoxy-hemoglobin density distribution, and a total hemoglobin density distribution.

15. The image generating apparatus according to claim 1, wherein the arithmetic unit is configured to perform two or more types of image reconstruction processing including the default and provisional image reconstruction processing.

16. A signal processing apparatus, comprising:
an arithmetic unit configured to:
obtain, from a storage unit, photoacoustic signal data generated by detecting a photoacoustic wave generated in an object in response to irradiation with light;
showing a plurality of candidates in image reconstruction processing including a time-domain image reconstruction processing, a Fourier-domain image reconstruction processing and a model base image reconstruction processing, those of which are ready to be specified by a user,
obtain information on a specified image reconstruction processing which is specified by the user, to be performed on the photoacoustic signal data;
generate image data by performing specified image reconstruction processing; and
cause a display unit to display a state of progress in the corresponding image reconstruction processing and an image based on the image data.

17. An image generating method, comprising:
obtaining photoacoustic signal data generated by detecting a photoacoustic wave generated in an object in response to irradiation with light,
showing a plurality of candidates in image reconstruction processing including a time-domain image reconstruction processing, a Fourier-domain image reconstruction processing and a model base image reconstruction processing, those of which are ready to be specified by a user,
obtaining information on a specified image reconstruction processing which is specified by a user, to be performed on the photoacoustic signal data,
generating image data by performing specified image reconstruction processing, and causing a display unit to display a state of progress in the corresponding image reconstruction processing and an image based on the image data.

18. A non-transitory computer-readable recording medium storing a program for executing the image generating method according to claim 17.

19. The image generating apparatus according to claim 1, wherein the image is displayed in association with the specified image reconstruction processing.

20. The image generating apparatus according to claim 1, wherein the arithmetic unit is configured to a remaining time in the corresponding image reconstruction processing.

* * * * *